(12) United States Patent
Li et al.

(10) Patent No.: US 6,890,717 B1
(45) Date of Patent: May 10, 2005

(54) OBP1: A NOVEL PROTEIN SELECTIVELY EXPRESSED IN OSTEOBLASTS

(75) Inventors: Yi-Ping Li, Brookline, MA (US); Wei Chen, Brookline, MA (US)

(73) Assignee: Forsyth Dental Infirmary for Children, Boston, MA (US)

( * ) Notice: Subject to any disclaimer, the term of this patent is extended or adjusted under 35 U.S.C. 154(b) by 207 days.

(21) Appl. No.: 09/724,304

(22) Filed: Nov. 28, 2000

(51) Int. Cl.[7] .................................................. C12Q 1/68
(52) U.S. Cl. ..................... 435/6; 435/68.1; 435/69.1; 435/440; 536/23.1; 536/24.1
(58) Field of Search .................... 435/6, 68.1, 69.1, 435/440; 536/23.1, 24.1

(56) References Cited

PUBLICATIONS

Bonaldo et al. Normalization and Substraction: Two approaches to facilitate gene discovery (1996) Genome Research 6: 791–806 (attachment: GenEmbl Data Base Search Copy ).*
GenBank Accession H41662 [online] , 1991.
GenBank Accession U37142 [online] , 1995.
GenBank Accession Q61361 [online] , 1997.
GenBank Accession U95102 [online] , 1999.
GenBank Accession AAA73926 [online] , 1995.
GenBank Accession AAB58159 [online] , 1997.
GenBank Accession P55068 [online] , 1994.
GenBank Accession X86406 [online] , 1995.
Aubin, Jane E., "Bone Stem Cells," *Journal of Cellular Biochemistry Supplements*, 30/31 : 73–82 (1998) .
Petersen, Donna N., et al., "Identification of Osteoblast/Osteocyte Factor 45 (OF45) , a Bone–specific cDNA Encoding an RGD–containing Protein That is Highly Expressed in Osteoblasts and Osteocytes," *The Journal of Biological Chemistry*, 275: 36172–36180 (2000) .
Bonaldo, M.F. et al., "Rattus norvegicus cDNA clone," DATABASE EBI Online! Database Accession No. AI059165 (1998) .
Malek, R.L. et al., "Rattus norvegicus cDNA," DATABASE EBI Online! Database Accession No. BF289422 (2000) .
Bonaldo, M.F. et al., "Rattus norvegicus cDNA clone," DATABASE EBI Online! Database Accession No. AI070352 (1998) , AI763821 (1999), AW531464 (1998).
Chambell, A.M., "Monoclonal Antibody Technology", *Elsevier Science Publishers B. V.*, Netherlands, 1984.

* cited by examiner

*Primary Examiner*—Long V. Le
*Assistant Examiner*—Jacob Cheu
(74) *Attorney, Agent, or Firm*—Ingrid A. Beattie; Mintz, Levin, Cohn, Ferris, Glovsky and Popeo, P.C.

(57) ABSTRACT

The invention provides nucleic acid molecules derived from human osteoblasts. The nucleic acid molecules are used in applications such as diagnostic methods, screening assays and as hybridization probes and primers.

11 Claims, 2 Drawing Sheets

210-22 Translation

```
cggtgccaataaatccttttaaaatataatttgaggggccgtggggtcaattgaccttta      60 tcttgcctgggggagggggggagttaggaagtaccagaacctgactttgggtaattgtgt     120 ttttaaaatacagaatgtcagagagcacatgtgcataggaacatgcggttgtgcacactt    180 gtgcacagatgcctggcgtattcatgcacctatataggtgccaacatccctagcctgctt    240 cctcagggggcctttaggacctgagccctgtcatcatttcagacatgggccttggccctg    300 agcagaggccaaggaagcATGAAGGTGCGTTCTAGGTCTTGTTTTCTCAGACCTGTTTTC    360
                  M  K  V  R  S  R  S  C  F  L  R  P  V  F     14

CCGTTGGGGGAGGCAGGAGGGGGCCGCAGTAATACTCCATCAAGCCCATTCCAGAGAGGA    420
 P  L  G  E  A  G  G  R  S  N  T  P  S  S  P  F  Q  R  G       34

GAGACACCCACCACACTCAGAACCTCCCAAGTATGTGAGGACTTTCCTTATGGGAACCCT    480
 E  T  P  T  T  L  R  T  S  Q  V  C  E  D  F  P  Y  G  N  P    54

GAGGTTCCCTCAGTTATTTCCTGCCTGAGAAGACAAGTCAGTCTTCCATCTCTGAGCCCA    540
 E  V  P  S  V  I  S  C  L  R  Q  V  S  L  P  S  L  S  P       74

GGTCTCCTAGTCTGAtagctggggcagcctctcccatttgcatgtctctttggtgcagc    600
 G  L  L  V  *                                                  79 cttgtaacctgaacatcagaaatgtggaagtggctgaacatgtaccaccaaccatccctg    660 cccagaccttaccacttcatgctttatcttctgataggattactcctaaccctgggccag    720 cctgactctcagcactgcatgtaggtgacagtgttgtgtgacttttatgggctgatgtg     780 attagaggtctgttcacaccagatagggcaccaaagacagtctgaagaaatgatcacacc    840 caaatctagctgcatccctggaagaccctcatccatgtcccatgttacaatctgcagg     900 ctgctttagctctagtgaagcggctcccttctctttgtaattgtttactgatggatgacc    960 tgggggtaggggttgtgaatttgtaactttgaactttctgctttcttatgaccctccctc   1020 cttcctccagggaggaattaaaaaaaaatgatgtgtttgcctgcaaaaaaaaaaaaaaa    1080 aaa                                                             1083
```

FIG. 1

Multiple Tissue Northern Blot Analysis of
OBP1 mRNA Expression

SEQUENCE LISTING

<160> NUMBER OF SEQ ID NOS: 2

<210> SEQ ID NO 1
<211> LENGTH: 1083
<212> TYPE: DNA
<213> ORGANISM: Homo sapiens

<400> SEQUENCE: 1

```
cggtgccaat aaatcctttt aaaatataat ttgaggggcc gtggggtcaa ttgaccttta      60
tcttgcctgg gggaggggg gagttaggaa gtaccagaac ctgactttgg gtaattgtgt     120
ttttaaaata cagaatgtca gagagcacat gtgcatagga acatgcggtt gtgcacactt     180
gtgcacagat gcctggcgta ttcatgcacc tatataggtg ccaacatccc tagcctgctt     240
cctcaggggg cctttaggac ctgagccctg tcatcatttc agacatgggc cttggccctg     300
agcagaggcc aaggaagcat gaaggtgcgt tctaggtctt gttttctcag acctgttttc     360
ccgttggggg aggcaggagg gggccgcagt aatactccat caagcccatt ccagagagga     420
gagacaccca ccacactcag aacctcccaa gtatgtgagg acttcctta tgggaaccct     480 gaggttccct cagttatttc ctgcctgaga agacaagtca gtcttccatc tctgagccca     540
ggtctcctag tctgatagct ggggcagcct ctcccatttt gcatgtctct ttggtgcagc     600
cttgtaacct gaacatcaga aatgtggaag tggctgaaca tgtaccacca accatccctg     660
cccagacctt accacttcat gctttatctt ctgataggat tactcctaac cctgggccag     720
cctgactctc agcactgcat gtaggtgaca gtgttgtgtg acttttttatg ggctgatgtg     780
```

-continued

```
attagaggtc tgttcacacc agatagggca ccaaagacag tctgaagaaa tgatcacacc      840
caaatctagc tgcatccctg gaagaccctc atcccatgtc cccatgttac aatctgcagg      900
ctgctttagc tctagtgaag cggctccctt ctctttgtaa ttgtttactg atggatgacc      960
tgggggtagg ggttgtgaat ttgtaacttt gaactttctg ctttcttatg accctccctc     1020
cttcctccag ggaggaatta aaaaaaaatg atgtgtttgc ctgcaaaaaa aaaaaaaaaa     1080
aaa                                                                  1083
```

<210> SEQ ID NO 2
<211> LENGTH: 78
<212> TYPE: PRT
<213> ORGANISM: Homo sapiens

<400> SEQUENCE: 2

```
Met Lys Val Arg Ser Arg Ser Cys Phe Leu Arg Pro Val Phe Pro Leu
  1               5                  10                  15

Gly Glu Ala Gly Gly Arg Ser Asn Thr Pro Ser Ser Pro Phe Gln
                 20                  25                  30

Arg Gly Glu Thr Pro Thr Thr Leu Arg Thr Ser Gln Val Cys Glu Asp
             35                  40                  45

Phe Pro Tyr Gly Asn Pro Glu Val Pro Ser Val Ile Ser Cys Leu Arg
         50                  55                  60

Arg Gln Val Ser Leu Pro Ser Leu Ser Pro Gly Leu Leu Val
 65                  70                  75
```

OBP1: A NOVEL PROTEIN SELECTIVELY EXPRESSED IN OSTEOBLASTS

GOVERNMENT SUPPORT

The invention was supported, in whole or in part, by grant DE-10887 from the National Institutes of Health. The U.S. Government has certain rights in the invention.

BACKGROUND OF THE INVENTION

Human bones are continuously remodelling through the repeated process of resorption and reconstitution. In the process, osteoblasts and osteoclasts are considered to be the cells mainly in charge of bone formation and bone resorption, respectively. Thus, bone formation is promoted by stimulating the growth, differentiation, or activation of osteoblasts. Osteoblasts differentiate into osteocytes which are cells surrounded by a mineralized matrix. Very little is known about the mechanisms directing the differentiation of the osteoprogenitors into osteoblasts, but it is clear that there is a fine balance between different cellular stages that control osteoblastic cell renewal and cell loss.

SUMMARY OF THE INVENTION

Using a subtractive differential screening approach, a full-length cDNA clone (clone #210-22, also known as clone #22) sequence which is selectively expressed in osteoblasts was isolated from a rat osteoblast library. The nucleotide sequence (SEQ ID NO: 1; FIG. 1) predicts an encoded protein of 79 amino acids (SEQ ID NO: 2; FIG. 1). The amino acid sequence from amino acid 14 to amino acid 57 is 42% identical to the mitotic phosphoprotein 90 and brevican core protein. Other amino acid sequences do not share any significant homology with the predicted protein. The gene and the protein encoded by the gene are herein designated OBP1.

Northern blot analysis of multiple tissues was performed using clone #22 cDNA 5/as a probe. As shown in FIG. 2, a 1 kB mRNA signal was detected very strongly in differentiated rat osteoblasts, but not in the other rat tissues assessed. These data demonstrate that OBP1 is selectively expressed in rat osteoblasts. This pattern of expression was previously observed with osteocalcin, a marker for osteoblast phenotype. Thus, OBP1 provides a marker for osteoblasts, and may also have an important regulatory function. Specific expression of OBP1 in differentiated osteoblasts indicates its possible role in bone formation, and thus altering OBP1 expression and/or activity may alter the process of bone formation. Accordingly, OBP1 may provide new diagnostic and therapeutic approaches to diseases involving altered bone resorption, such as osteoporosis and periodontal disease.

Thus, the present invention relates to an isolated nucleic acid molecule comprising a nucleotide sequence selected from the group consisting of SEQ ID NO: 1; the complement of SEQ ID NO: 1; nucleotides 319–555 of SEQ ID NO: 1; and the complement of nucleotides 319–555 of SEQ ID NO: 1. That is, the invention relates to nucleic acid molecules comprising the coding region (nucleotides 319–555 of SEQ ID NO: 1) of the OBP1 gene or comprising the complete cDNA sequence (SEQ ID NO: 1) of the OBP1 gene. The invention also relates to an isolated nucleic acid molecule consisting of or consisting essentially of a nucleotide sequence selected from the group consisting of SEQ ID NO: 1; the complement of SEQ ID NO: 1; nucleotides 319–555 of SEQ ID NO: 1; and the complement of nucleotides 319–555 of SEQ ID NO: 1. The invention also relates to a nucleic acid molecule comprising a nucleotide sequence which encodes the amino acid sequence of SEQ ID NO: 2.

The invention further relates to a nucleic acid molecule which hybridizes under high stringency conditions to a nucleotide sequence selected from the group consisting of SEQ ID NO: 1; the complement of SEQ ID NO: 1; nucleotides 319–555 of SEQ ID NO: 1; and the complement of nucleotides 319–555 of SEQ ID NO: 1.

The invention further provides a method for assaying the presence of a nucleic acid molecule in a sample, comprising contacting said sample with a second nucleic acid molecule comprising a nucleotide sequence selected from the group consisting of SEQ ID NO: 1; the complement of SEQ ID NO: 1; nucleotides 319–555 of SEQ ID NO: 1; and the complement of nucleotides 319–555 of SEQ ID NO: 1, under conditions appropriate for selective hybridization (e.g., under high stringency hybridization conditions) of the second nucleic acid molecule to a complementary nucleic acid molecule in the sample. Using this method, the nucleic acid molecules of the invention can be used to identify the presence of a complementary nucleic acid molecule in a sample. Complementary nucleic acid molecules can include perfectly complementary nucleic acid molecules as well as highly complementary nucleic acid molecules (i.e., nucleic acid molecules which are sufficiently complementary to hybridize to the nucleic acid molecules of the invention under high stringency hybridization conditions).

The invention also relates to a vector comprising an isolated nucleic acid molecule of the invention operatively linked to a regulatory sequence, as well as to a recombinant host cell comprising the vector. The invention also provides a method for preparing a polypeptide encoded by an isolated nucleic acid molecule, comprising culturing a recombinant host cell of the invention under conditions suitable for expression of said nucleic acid molecule.

The invention further provides an isolated polypeptide encoded by isolated nucleic acid molecules of the invention. In a particular embodiment, the polypeptide comprises the amino acid sequence of SEQ ID NO: 2. The invention also relates to an isolated polypeptide comprising an amino acid sequence which is greater than about 80 percent identical to the amino acid sequence of SEQ ID NO: 2.

The invention also relates to an antibody, or an antigen-binding fragment thereof, which selectively binds to the polypeptides of the invention, as well as to a method for assaying the presence of a polypeptide encoded by an isolated nucleic acid molecule of the invention in a sample, comprising contacting said sample with an antibody which specifically binds to the encoded polypeptide.

BRIEF DESCRIPTION OF THE DRAWINGS

FIG. 1 shows the nucleotide sequence (SEQ ID NO: 1) of OBP1 cDNA and the deduced amino acid sequence (SEQ ID NO: 2) of OBP1.

DETAILED DESCRIPTION OF THE INVENTION

Figure 2:
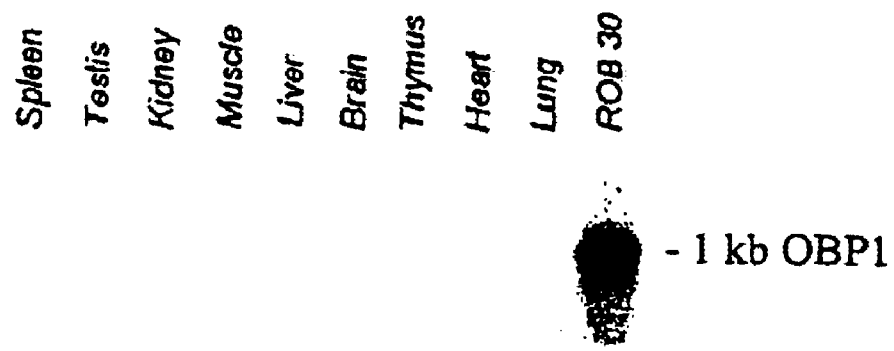
FIG. 2 shows a multiple tissue Northern blot analysis of OBP1 mRNA expression.

As described in detail herein, the invention relates to an isolated nucleic acid molecule which is selectively expressed in osteoblasts. In one embodiment, the invention relates to an isolated nucleic acid molecule having the nucleotide sequence of SEQ ID NO: 1, or a portion thereof (e.g., nucleotides 319–555 of SEQ ID NO: 1). The invention also relates to an isolated nucleic acid molecule which encodes the amino acid sequence of SEQ ID NO: 2, or a portion thereof.

As appropriate, the isolated nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. The nucleic acid molecule can include all or a portion of the coding sequence of a gene and can further comprise additional non-coding sequences such as introns and non-coding 3' and 5' sequences (including regulatory sequences, for example). Additionally, the nucleic acid molecule can be fused to a marker sequence, for example, a sequence that encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from influenza.

An "isolated" nucleic acid molecule, as used herein, is one that is separated from nucleic acids which normally flank the nucleic acid molecule in nature. With regard to genomic DNA, the term "isolated" refers to nucleic acid molecules which are separated from the chromosome with which the genomic DNA is naturally associated. For example, the isolated nucleic acid molecule can contain less than about 5 kb, 4 kb, 3 kb, 2 kb, 1 kb, 0.5 kb or 0.1 kb of nucleotides which flank the nucleic acid molecule in the genomic DNA of the cell from which the nucleic acid molecule is derived.

Moreover, an isolated nucleic acid molecule of the invention, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid molecule comprises at least about 50, 80 or 90% (on a molar basis) of all macromolecular species present.

Further, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. In one embodiment, the variants hybridize under high stringency hybridization conditions (e.g., for selective hybridization) to a nucleotide sequence comprising a nucleotide sequence of the invention.

Stringent hybridization conditions for nucleic acid molecules are well known to those skilled in the art and can be found in standard texts such as *Current Protocols in Molecular Biology*, John Wiley & Sons, N.Y. (1998), pp. 2.10.1–2.10.16 and 6.3.1–6.3.6, the teachings of which are hereby incorporated by reference. As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another. In one non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, preferably at least 40%, more preferably at least 60%, and even more preferably at least 70%, 80% or 90% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873–5877 (1993). Such an algorithm is incorporated into the NBLAST and XBLAST programs (version 2.0) as described in Altschul et al., *Nucleic Acids Res.*, 25:389–3402 (1997). When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.*, 10:3–5; and FASTA described in Pearson and Lipman (1988) *PNAS*, 85:2444–8.

In another embodiment, the percent identity between two amino acid sequences can be accomplished using the GAP program in the CGC software package using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the CGC software package, using a gap weight of 50 and a length weight of 3.

The present invention also provides isolated nucleic acid molecules that contain a fragment or portion that hybridizes under highly stringent conditions to a nucleotide sequence comprising a nucleotide sequence of the invention. The nucleic acid fragments of the invention are at least about 15, preferably at least about 18, 20, 23 or 25 nucleotides, and can be 30, 40, 50, 100, 200 or more nucleotides in length. Longer fragments, for example, 30 or more nucleotides in length, which encode antigenic proteins or polypeptides described herein are useful.

In a related aspect, the nucleic acid fragments of the invention are used as probes or primers in assays such as those described herein. "Probes" are oligonucleotides that hybridize in a base-specific manner to a complementary strand of nucleic acid molecules. Such probes include polypeptide nucleic acids, as described in Nielsen et al., *Science*, 254, 1497–1500 (1991). Typically, a probe comprises a region of nucleotide sequence that hybridizes under highly stringent conditions to at least about 15, typically about 20–25, and more typically about 40, 50 or 75, consecutive nucleotides of a nucleic acid molecule comprising a nucleotide sequence of the invention. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides.

The nucleic acid molecules of the invention such as those described above can be identified and isolated using standard molecular biology techniques and the sequence information provided in SEQ ID NO: 1. For example, nucleic acid molecules can be amplified and isolated by the polymerase chain reaction using synthetic oligonucleotide primers designed based on one or more of the sequences provided in SEQ ID NO: 1, the complement of SEQ ID NO: 1, nucleotides 319–555 of SEQ ID NO: 1, the complement of nucleotides 319–555 of SEQ ID NO: 1 and other portions of SEQ ID NO: 1 and its complement. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.*, 19:4967 (1991); Eckert et al., *PCR Methods and Applications*, 1:17 (1991); *PCR* (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics*, 4:560 (1989), Landegren et al., *Science*, 241:1077 (1988), transcription amplification (Kwoh et al., *Proc. Natl. Acad. Sci. USA*, 86:1173 (1989)), and self-sustained sequence replication (Guatelli et al., *Proc. Nat. Acad. Sci. USA*, 87;1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a cDNA library derived from osteoblasts, e.g., human osteoblasts, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a protein of the appropriate molecular weight. For example, the direct analysis of the nucleotide sequence of nucleic acid molecules of the present invention can be accomplished using well-known methods that are commercially available. See, for example, Sambrook et at., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein and the DNA encoding the protein can be isolated, sequenced and further characterized.

Antisense nucleic acid molecules of the invention can be designed using the nucleotide sequences of the invention, and constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

In general, the isolated nucleic acid sequences can be used as molecular weight markers on Southern gels, and as chromosome markers which are labeled to map related gene positions. The nucleic acid sequences can also be used to compare with endogenous DNA sequences in patients to identify genetic disorders, and as probes, such as to hybridize and discover related DNA sequences or to subtract out known sequences from a sample. The nucleic acid sequences can further be used to derive primers for genetic fingerprinting, to raise anti-protein antibodies using DNA immunization techniques, and as an antigen to raise anti-DNA antibodies or elicit immune responses. Additionally, the nucleotide sequences of the invention can be used to identify and express recombinant proteins for analysis, characterization or therapeutic use, or as markers for tissues in which the corresponding protein is expressed, either constitutively, during tissue differentiation, or in diseased states.

The present invention also has utility for the production and identification of nucleic acid probes useful for identifying OBP1 DNA, including genomic DNA. Due to the specificity of expression of OBP1 in osteoblasts, nucleic acid molecules, polypeptides and antibodies described herein are also useful for identifying osteoblasts using well established techniques. Nucleic acid molecules of the present invention are also useful in gene therapy. For example, they can be used to alter the expression, e.g., in osteoblasts, of an aberrant OBP1 gene product, or to correct aberrant expression of OBP1. The sequences described herein can further be used to cause OBP1 expression in cells in which such expression does not ordinarily occur, e.g., in cells which are not osteoblasts.

Another aspect of the invention pertains to nucleic acid constructs containing a nucleic acid moleucle selected from the group consisting of SEQ ID NO: 1 and the complement of SEQ ID NO: 1 (or a portion thereof). The constructs comprise a vector (e.g., an expression vector) into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed and the level of expression of protein desired. The expression vectors of the invention can be introduced into host cells to thereby produce proteins or peptides, including fusion proteins or peptides, encoded by nucleic acid molecules as described herein.

The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid molecule of the invention has been introduced. Such host cells can then be used to create non-human transgenic animals in which exogenous nucleotide sequences have been introduced into the genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens and amphibians. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Methods for constructing homologous recombination vectors and homologous recombinant animals are described further in Bradley (1991) *Current Opinion in Bio/Technology*, 2:823–829 and in PCT Publication Nos. WO 90/11354, WO 91/01140, WO 92/0968, and WO 93/04169. Clones of the non-human transgenic animals described herein can also be produced according to the methods described in Wilmut et al. (1997) *Nature*, 385:810–813 and PCT Publication Nos. WO 97/07668 and WO 97/07669.

The present invention also provides isolated polypeptides and variants and fragments thereof that are encoded by the nucleic acid molecules of the invention. For example, as described above, the nucleotide sequences can be used to design primers to clone and express cDNAs encoding the polypeptides of the invention. In one embodiment, the polypeptide comprises the amino acid sequence of SEQ ID NO: 2 or a portion thereof.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified."

The polypeptides of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the protein preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide comprises an amino acid sequence encoded by a nucleic acid molecule comprising a nucleotide sequence selected from the group consisting of SEQ ID NO: 1 and complements and portions thereof, e.g., SEQ ID NO: 2 or a portion thereof. However, the invention also encompasses sequence variants. Variants include a substantially homologous protein encoded by the same genetic locus in an organism, i.e., an allelic variant. Variants also encompass proteins derived from other genetic loci in an organism, but having substantial homology to a polypeptide encoded by a nucleic acid molecule comprising a nucleotide sequence selected from the group consisting of SEQ ID NO: 1 and complements and portions thereof. Variants also include proteins substantially homologous or identical to these polypeptides but derived from another organism, i.e., an ortholog. Variants also include proteins that are substantially homologous or identical to these polypeptides that are produced by chemical synthesis. Variants also include proteins that are substantially homologous or identical to these polypeptides that are produced by recombinant methods.

As used herein, two proteins (or a region of the proteins) are substantially homologous or identical when the amino acid sequences are at least about 45–55%, typically at least about 70–75%, more typically at least about 80–85%, and most typically greater than about 93% or more homologous or identical. A substantially homologous amino acid sequence, according to the present invention, will be encoded by a nucleic acid molecule hybridizing to SEQ ID NO: 1, or portion thereof, under stringent conditions as more particularly described above.

To determine the percent homology or identity of two amino acid sequences, or of two nucleic acid sequences, the sequences are aligned for optimal comparison purposes (e.g., gaps can be introduced in the sequence of one protein or nucleic acid molecule for optimal alignment with the other protein or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses polypeptides having a lower degree of identity but having sufficient similarity so as to perform one or more of the same functions performed by a polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306–1310 (1990).

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al, Science, 244:1081–1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., J. Mol. Biol., 224:899–904 (1992); de Vos et al Science, 255:306–312 (1992)).

The invention also includes polypeptide fragments of the polypeptides of the invention. Fragments can be derived from a polypeptide encoded by a nucleic acid molecule comprising SEQ ID NO: 1 or a portion thereof and the complements thereof. However, the invention also encompasses fragments of the variants of the polypeptides described herein. As used herein, a fragment comprises at least 6 contiguous amino acids. Useful fragments include those that retain one or more of the biological activities of the polypeptide as well as fragments that can be used as an immunogen to generate polypeptide-specific antibodies.

Biologically active fragments (peptides which are, for example, 6, 9, 12, 15, 16, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion proteins. These comprise a polypeptide of the invention operatively linked to a heterologous protein having an amino acid sequence not substantially homologous to the polypeptide. "Operatively linked" indicates that the polypeptide protein and the heterologous protein are fused in-frame. The heterologous protein can be fused to the N-terminus or C-terminus of the polypeptide. In one embodiment the fusion protein does not affect function of the polypeptide per se. For example, the fusion protein can be a GST-fusion protein in which the polypeptide sequences are fused to the C-terminus of the GST sequences. Other types of fusion proteins include, but are not limited to, enzymatic fusion proteins, for example beta-galactosidase fusions, yeast two-hybrid GAL fusions, poly-His fusions and Ig fusions. Such fusion proteins, particularly poly-His fusions, can facilitate the purification of recombinant polypeptide. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al., Journal of Molecular Recognition, 8:52–58 (1995) and Johanson et al., The Journal of Biological Chemistry, 270, 16:9459–9471 (1995). Thus, this invention also encompasses soluble fusion proteins containing a polypeptide of the invention and various portions of the constant regions of heavy or light chains of immunoglobulins of various subclass (IgG, IgM, IgA, IgE).

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed and re-amplified to generate a chimeric nucleic acid sequence (see Ausubel et al., Current Protocols in Molecular Biology, 1992). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide protein.

The isolated polypeptide can be purified from cells that naturally express it, such as from osteoblasts, purified from cells that have been altered to express it (recombinant), or synthesized using known protein synthesis methods. In one embodiment, the protein is produced by recombinant DNA techniques. For example, a nucleic acid molecule encoding the polypeptide is cloned into an expression vector, the expression vector introduced into a host cell and the protein expressed in the host cell. The protein can then be isolated from the cells by an appropriate purification scheme using standard protein purification techniques.

In general, polypeptides or proteins of the present invention can be used as a molecular weight marker on SDS- PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the protein or a molecule to which it binds (e.g., a receptor or a ligand) in biological fluids. The polypeptides can also be used as markers for cells or tissues in which the corresponding protein is preferentially expressed, either constitutively, during tissue differentiation, or in a diseased state. The polypeptides can be used to isolate a corresponding binding partner, e.g., receptor or ligand, such as, for example, in an interaction trap assay, and to screen for peptide or small molecule antagonists or agonists of the binding interaction.

In another aspect, the invention provides antibodies to the polypeptides and polypeptide fragments of the invention, e.g., having an amino acid sequence encoded by a nucleic acid molecule comprising all or a portion of SEQ ID NO: 1. The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g. a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature*, 256:495–497, the human B cell hybridoma technique (Kozbor et al. (1983) *Immunol. Today*, 4:72), the EBV-hybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al. (1977) *Nature*, 266:55052; R. H. Kenneth, in *Monoclonal Antibodies: A New Dimension In Biological Analyses*, Plenum Publishing Corp., New York, N.Y. (1980); and Lerner (1981) *Yale J. Biol. Med.*, 54:387402. Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology*, 9:1370–1372; Hay et al. (1992) *Hum. Antibod. Hybridomas*, 3:81–85; Huse et al. (1989) *Science*, 246:1275–1281; Griffiths et al. (1993) *EMBO J.*, 12:725–734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials.

Portions or fragments of the nucleotide sequences identified herein (and the corresponding complete gene sequences) can be used in numerous ways as polynucleotide reagents. For example, these sequences can be used to: (i)

map their respective genes on a chromosome; and, thus, locate gene regions associated with genetic disease; (ii) identify an individual from a minute biological sample (tissue typing); and (iii) aid in forensic identification of a biological sample.

The present invention also pertains to diagnostic assays for determining protein and/or nucleic acid expression as well as activity of proteins of the invention, in the context of a biological sample (e.g., blood, serum, cells, tissue) to thereby determine whether an individual is afflicted with a disease or disorder, or is at risk of developing a disorder, associated with aberrant expression or activity. The invention also provides for prognostic (or predictive) assays for determining whether an individual is at risk of developing a disorder associated with activity or expression of proteins or nucleic acid molecules of the invention.

Disorders which may be treated or diagnosed by methods described herein include, but are not limited to, diseases characterized by an increase in bone density, including osteopetrosis, osteosclerosis, pyknodysostosis, osteomyelosclerosis, hyperphosphatasia, progressive diaphyseal dysplasia, melorheostosis, osteopoikilosis, hyperostosis frontalis interna, sclerostosis, McCune-Albright syndrome and spondyloepiphyseal dysplasia; disorders characterized by a decrease in bone density, including osteoarthritis, Maroteaux-Lamy syndrome and osteoporosis; and disorders of bone formation, including osteogenisis imperfecta, sutural craneosynostosis, osteomalacia and cleidocranial dysplasia, and bone cancers such as osteosarcomas. Additionally, the methods described herein may be useful for the treatment or diagnosis of bone disorders associated with cancer, anorexia nervosa, and auto-immune disorders. Furthermore, the invention provides for the treatment of diseases characterized by primary changes in osteoblastic cell function/activity (e.g., ossifying fibroma and fibrous dysplasia, osteoblastoma and osteoid osteoma, and osteosarcoma) and diseases or systemic conditions affecting bone in which abnormal osteoblastic cell function/activity is a secondary effect (e.g., acromegaly, hypercalcemia, primary or secondary hyperparathyroidism, hyperthyroidism, or Paget's disease of bone). In addition, the invention can be used to treat diseases associated with localized changes in bone metabolism in which abnormal osteoblastic cell function/activity contributes to pathogenic bone changes. For example, the invention can be used to treat periodontal disease (localized, inflammation-induced bone loss), rheumatoid arthritis and osteoarthritis (localized, inflammation-induced bone loss) localized osteoporosis, mastocytosis, multiple myeloma, and bone metastases of various tumors.

For example, mutations in a specified gene can be assayed in a biological sample. Such assays can be used for prognostic or predictive purpose to thereby prophylactically treat an individual prior to the onset of a disorder characterized by or associated with expression or activity of nucleic acid molecules or proteins of the invention.

Another aspect of the invention pertains to monitoring the influence of agents (e.g., drugs, compounds) on the expression or activity of proteins of the invention in clinical trials.

These and other agents are described in further detail in the following sections.

1. Diagnostic Assays

An exemplary method for detecting the presence or absence of proteins or nucleic acid molecules of the invention in a biological sample involves obtaining a biological sample from a test subject and contacting the biological sample with a compound or an agent capable of detecting the protein, or nucleic acid molecule (e.g., mRNA, genomic DNA) that encodes the protein, such that the presence of the protein or nucleic acid molecule is detected in the biological sample. A preferred agent for detecting mRNA or genomic DNA is a labeled nucleic acid probe capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA or genomic DNA. For example, the nucleic acid probe can be all or a portion of SEQ ID NO: 1, or the complement of SEQ ID NO: 1, or a portion thereof. Other suitable probes for use in the diagnostic assays of the invention are described herein.

In one embodiment, the agent for detecting proteins of the invention is an antibody capable of binding to the protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, calls and biological fluids isolated from a subject, as well as tissues, cells and fluids present within a subject. That is, the detection method of the invention can be used to detect mRNA, protein, or genomic DNA of the invention in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled anti-protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample or lung tissue biopsy isolated by conventional means from a subject.

In another embodiment, the methods further involve obtaining a control biological sample from a control subject, contacting the control sample with a compound or agent capable of detecting protein, mRNA, or genomic DNA of the invention, such that the presence of protein, mRNA or genomic DNA is detected in the biological sample, and comparing the presence of protein, mRNA or genomic DNA in the control sample with the presence of protein, mRNA or genomic DNA in the test sample.

The invention also encompasses kits for detecting the presence of proteins or nucleic acid molecules of the invention in a biological sample. For example, the kit can comprise a labeled compound or agent capable of detecting protein or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid molecules.

The diagnostic methods described herein can furthermore be utilized to identify subjects having or at risk of developing a disease or disorder associated with aberrant expression or activity of proteins and nucleic acid molecules of the invention. For example, the assays described herein, such as the preceding diagnostic assays or the following assays can be utilized to identify a subject having or at risk of developing a disorder associated with protein or nucleic acid expression or activity such as a proliferative disorder, a differentiative or developmental disorder, or a hematopoietic disorder. Alternatively, the prognostic assays can be utilized to identify a subject having or at risk for developing a differentiative or proliferative disease (e.g., cancer) particularly of the bones. Thus, the present invention provides a method for identifying a disease or disorder associated with aberrant expression or activity of proteins or nucleic acid molecules of the invention, in which a test sample is obtained from a subject and protein or nucleic acid molecule (e.g., mRNA, genomic DNA) is detected, wherein the presence of protein or nucleic acid molecule is diagnostic for a subject having or at risk of developing a disease or disorder associated with aberrant expression or activity of the protein or nucleic acid sequence of the invention. As used herein, a "test sample" refers to a biological sample obtained from a subject of interest. For example, a test sample can be a biological fluid (e.g., serum), cell sample (e.g., osteoblasts), or tissue sample.

The invention provides a method (also referred to herein as a "screening assay") for identifying modulators, i.e., candidate or test compounds or agents (e.g., antisense, polypeptides, peptidomimetics, small molecules or other drugs) which bind to nucleic acid molecules, polypeptides or proteins described herein or have a stimulatory or inhibitory effect on, for example, expression or activity of the nucleic acid molecules, polypeptides or proteins of the invention.

In one embodiment, the invention provides assays for screening candidate or test compounds that bind to or modulate the activity of protein or polypeptide described herein or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.,* 12:145).

In one embodiment, an assay is a cell-based assay in which a cell that expresses an encoded polypeptide (e.g., cell surface protein such as a receptor) is contacted with a test compound and the ability of the test compound to bind to the polypeptide is determined. The cell, for example, can be of mammalian origin, such as from osteoblasts. Determining the ability of the test compound to bind to the polypeptide can be accomplished, for example, by coupling the test compound with a radioisotope or enzymatic label such that binding of the test compound to the polypeptide can be determined by detecting the labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a test compound to interact with the polypeptide without the labeling of any of the interactants. For example, a microphysiometer can be used to detect the interaction of a test compound with the polypeptide without the labeling of either the test compound or the polypeptide. McConnell, H. M. et al. (1992) *Science,* 257:1906–1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and polypeptide.

In one embodiment, the assay comprises contacting a cell which expresses an encoded protein described herein on the cell surface (e.g., a receptor) with a polypeptide ligand or biologically-active portion thereof, to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide as compared to the ability of the ligand, or a biologically active portion thereof, to bind to the polypeptide.

In another embodiment, an assay is a cell-based assay comprising contacting a cell expressing a particular target molecule described herein with a test compound and determining the ability of the test compound to modulate or alter (e.g. stimulate or inhibit) the activity of the target molecule. Determining the ability of the test compound to modulate the activity of the target molecule can be accomplished, for example, by determining the ability of a known ligand to bind to or interact with the target molecule.

In yet another embodiment, an assay of the present invention is a cell-free assay in which protein of the invention or biologically active portion thereof is contacted with a test compound and the ability of the test compound to bind to the protein or biologically active portion thereof is determined. Binding of the test compound to the protein can be determined either directly or indirectly as described above. In one embodiment, the assay includes contacting the protein or biologically active portion thereof with a known compound which binds the protein to form an assay mixture, contacting the assay mixture with a test compound, and determining the ability of the test compound to interact with the protein. Determining the ability of the test compound to interact with the protein comprises determining the ability of the test compound to preferentially bind to the protein or biologically active portion thereof as compared to the known compound.

In another embodiment, the assay is a cell-free assay in which a protein of the invention or biologically active portion thereof is contacted with a test compound and the ability of the test compound to modulate or alter (e.g., stimulate or inhibit) the activity of the protein or biologically active portion thereof is determined. Determining the ability of the test compound to modulate the activity of the protein can be accomplished, for example, by determining the ability of the protein to bind to a known target molecule by one of the methods described above for determining direct binding. In an alternative embodiment, determining the ability of the test compound to modulate the activity of a protein of the invention can be accomplished by determining the ability of the protein to further modulate the activity of a target molecule. For example, the catalytic/enzymatic activity of the target molecule on an appropriate substrate can be determined as previously described.

In yet another embodiment, the cell-free assay involves contacting a protein of the invention or biologically active portion thereof with a known compound which binds the protein to form an assay mixture, contacting the assay mixture with a test compound, and determining the ability of the test compound to interact with the protein, wherein determining the ability of the test compound to interact with the protein comprises determining the ability of the protein to preferentially bind to or modulate the activity of a target molecule.

In more than one embodiment of the above assay methods of the present invention, it may be desirable to immobilize either the protein or its target molecule to facilitate separation of complexed from uncomplexed forms of one or both of the proteins, as well as to accommodate automation of the assay. Binding of a test compound to the protein, or interaction of the protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided which adds a domain that allows one or both of the proteins to be bound to a matrix.

In another embodiment, modulators of expression of nucleic acid molecules of the invention are identified in a method wherein a cell is contacted with a candidate compound and the expression of appropriate mRNA or protein in the cell is determined. The level of expression of appropriate mRNA or protein in the presence of the candidate compound is compared to the level of expression of mRNA or protein in the absence of the candidate compound. The candidate compound can then be identified as a modulator of expression based on this comparison. For example, when expression of mRNA or protein is greater (statistically significantly greater) in the presence of the candidate compound than in its absence, the candidate compound is identified as a stimulator or enhancer of the mRNA or protein expression. Alternatively, when expression of the mRNA or protein is less (statistically significantly less) in the presence of the candidate compound than in its absence, the candidate compound is identified as an inhibitor of the mRNA or protein expression. The level of mRNA or protein expression in the cells can be determined by methods described herein for detecting mRNA or protein.

This invention further pertains to novel agents identified by the above-described screening assays. Accordingly, it is within the scope of this invention to further use an agent identified as described herein in an appropriate animal model. For example, an agent identified as described herein (e.g., a modulating agent, an antisense nucleic acid molecule, a specific antibody, or a protein-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present invention provides for both prophylactic and therapeutic methods of treating a subject at risk of (or susceptible to) a disorder or having a disorder associated with aberrant expression or activity of proteins or nucleic acid molecules of the invention. In one aspect, the invention provides a method for preventing in a subject, a disease or condition associated with aberrant expression or activity of genes or proteins of the present invention, by administering to the subject an agent which modulates expression or at least one activity of a gene or protein of the invention. Subjects at risk for a disease that is caused or contributed to by aberrant gene expression or protein activity can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein.

Another aspect of the invention pertains to methods of modulating expression or activity of genes or proteins of the invention for therapeutic purposes. The modulatory method of the invention involves contacting a cell with an agent that modulates one or more of the activities of the specified protein associated with the cell. An agent that modulates protein activity can be an agent as described herein, such as a nucleic acid molecule or a protein, a naturally-occurring target molecule of a protein described herein, a polypeptide, a peptidomimetic, or other small molecule. In one embodiment, the agent stimulates one or more protein activities. Examples of such stimulatory agents include active protein as well as a nucleic acid molecule encoding the protein that has been introduced into the cell. In another embodiment, the agent inhibits one or more protein activities. Examples of such inhibitory agents include antisense nucleic acid molecules and anti-protein antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a protein or nucleic acid molecule of the invention. In one embodiment, the method involves administering an agent (e.g., an agent identified by a screening assay described herein), or combination of agents that modulates (e.g., upregulates or downregulates) expression or activity of a gene or protein of the invention. In another embodiment, the method involves administering a protein or nucleic acid molecule of the invention as therapy to compensate for reduced or aberrant expression or activity of the protein or nucleic acid molecule.

Stimulation of protein activity is desirable in situations in which the protein is abnormally downregulated and/or in which increased protein activity is likely to have a beneficial effect. Likewise, inhibition of protein activity is desirable in situations in which the protein is abnormally upregulated and/or in which decreased protein activity is likely to have a beneficial effect. One example of such a situation is where a subject has a disorder characterized by aberrant development or cellular differentiation. The molecules of the present invention, as well as agents, or modulators which have a stimulatory or inhibitory effect on the protein activity (e.g., gene expression) as identified by a screening assay described herein can be administered to individuals to treat (prophylactically or therapeutically) disorders (e.g., proliferative or developmental disorders) associated with aberrant protein activity.

The invention will be further described by the following non-limiting examples. The teachings of all publications cited herein are incorporated herein by reference in their entirety.

EXAMPLES

Subtractive Probe Preparation

Five μg of E9.5 embryo head mRNA (i.e., the source of the pre-osteoblast) was reverse-transcribed using random primers. A reaction was carried out at 42° C. for 1 hour with $^{32}$PACTP incorporation. After precipitation, reaction products were resuspended in 0.1 M NaOH and incubated for 20 minutes at 65° C. to hydrolyze RNA templates. Probes were neutralized with 0.1 acetic acid and size fractionated on Sephadex G-50. Biotinylated RNA as "driver" was prepared from E9.5 embryo body without the head (i.e., only the trunk). cDNA probes were hybridized with a ten-fold excess of biotinylated mRNA. The precipitated cDNA-RNA mixtures were resuspended in 10 to 20 μl of $H_2O$ and heated to 100° C. for 1 minute. An equal volume of 2× hybridization buffer (12×SSC containing 1.0% sodium dodecylsulfate) was added, and the mixture was incubated at 65° C. for 2 to 24 hours. Following addition of an equal volume of HEPES buffer (10 mM HEPES; pH 7.5, 1 mM EDTA), 20 μg of streptavidin was added and the mixture was incubated on ice for 10 minutes. Biotinylated RNA and RNA-cDNA duplexes, complexed with avidin, were removed by repeated phenol-chloroform extractions. Aqueous-phase cDNA probes ("subtractive probes") were precipitated with ethanol and subjected to a second round of subtraction as described above, under identical conditions, prior to use in differential screening.

Differential Screening

A total of $5 \times 10^5$ clones from osteoblast cDNA library (Lambda-ZAP System, Stratagene) were screened in this study. Duplicate filters were made from 145 mm plates containing $1 \times 10^4$ recombinant bacteriophage each by plaque lifts, and these were hybridized in parallel using equal amounts of the subtracted probes or the control probes that were derived from the animal trunk. The filters were hybridized, washed and exposed to films. Head (source of pre-osteoblast)-specific clones were identified by overlaying films from corresponding filters. Clones selected in the primary screening were re-screened once at low density to verify differential expression and for plaque purification.

Sequence Analysis

OBP1 cDNA clones were sequenced using an ABI377 sequencer. Nucleotide sequences were compared by the BLAST algorithm with known sequences resident in the National Center for Biotechnology Information databases.

Northern Hybridization

Northern hybridization was used to confirm the results from subtractive-differential screening, and to determine the tissue and cellular distribution, size and amount of OBP1.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An isolated nucleic acid molecule comprising the nucleotide sequence of SEQ ID NO: 1.

2. An isolated nucleic acid molecule according to claim 1 which is DNA.

3. An isolated nucleic acid molecule comprising the nucleotide sequence of the complement of SEQ ID NO: 1.

4. An isolated nucleic acid molecule comprising an isolated coding region of the nucleotide sequence of SEQ ID NO:1, wherein said isolated coding region comprises nucleotides 319–555 of SEQ ID NO: 1.

5. An isolated nucleic acid molecule which encodes the amino acid sequence of SEQ ID NO: 2.

6. A vector comprising an isolated nucleic acid molecule according to claim 1 operatively linked to a regulatory sequence.

7. A recombinant host cell comprising the vector of claim 6.

8. A method for preparing a polypeptide encoded by an isolated nucleic acid molecule, comprising culturing the recombinant host cell of claim 7 under conditions suitable for expression of said nucleic acid molecule and isolating the polypeptide encoded by the expressed nucleic acid.

9. An isolated polypeptide encoded by an isolated nucleic acid molecule according to claim 1.

10. An isolated polypeptide comprising the amino acid sequence of SEQ ID NO: 2.

11. An isolated nucleic acid molecule comprising a complementary nucleotide sequence for an isolated coding region of the nucleotide sequence of SEQ ID NO:1, wherein said isolated coding region comprises the complementary sequence of nucleotides 319–555 of SEQ ID NO: 1.

* * * * *